US005486760A

United States Patent [19]

Selleri et al.

[11] Patent Number: 5,486,760
[45] Date of Patent: Jan. 23, 1996

[54] APPARATUS FOR CHECKING SURFACE FEATURES OF CONICAL PARTS INCLUDING A PROBE DISPOSED WITHIN A TRANSVERSAL GROOVE OF A ROLLER

[75] Inventors: Narciso Selleri, Monteveglio; Giuliano Longhi, Bologna, both of Italy

[73] Assignee: Marposs Societa' Per Azioni, Bentivoglio, Italy

[21] Appl. No.: 162,151

[22] PCT Filed: Jul. 1, 1992

[86] PCT No.: PCT/EP92/01484

§ 371 Date: Dec. 13, 1993

§ 102(e) Date: Dec. 13, 1993

[87] PCT Pub. No.: WO93/01493

PCT Pub. Date: Jan. 21, 1993

[30] Foreign Application Priority Data

Jul. 4, 1991 [IT] Italy .................. BO91A0240

[51] Int. Cl.⁶ .......................... G01R 33/038; G01N 21/01
[52] U.S. Cl .............................. 324/262; 356/240
[58] Field of Search ............... 324/228, 237, 324/238, 240, 241, 242, 234, 236, 239, 243, 262; 356/237, 240

[56] References Cited

U.S. PATENT DOCUMENTS 3,260,390  7/1966  Morain .
3,787,983  1/1974  Diem .
3,896,646  7/1975  Lange ........................... 324/238
4,226,539  10/1980  Nakagawa et al. .
4,258,319  3/1981  Shimada et al. ................ 324/262
4,496,056  1/1985  Schoenig, Jr. et al. ......... 209/539
4,916,394  4/1990  Thompson ..................... 324/262
5,066,913  11/1991  Catanese ........................ 324/262
5,124,641  6/1992  Netter et al. .................. 324/262

FOREIGN PATENT DOCUMENTS 005019  10/1979  European Pat. Off. .
090304  3/1983  European Pat. Off. .

*Primary Examiner*—Sandra L. O'Shea
*Assistant Examiner*—Roger Phillips
*Attorney, Agent, or Firm*—Dickstein, Shapiro & Morin

[57] ABSTRACT

An apparatus for checking the outer surface of conical parts is presented. The apparatus comprises two substantially cylindrical feeding rollers adapted to support a plurality of the parts arranged in a row. The feeding rollers define convergent geometrical axes about which the rollers rotate in the same direction and have external surfaces made of materials with a different coefficient of friction. The rotation of the feeding rollers causes the parts to rotate about their own geometrical axes and the row of parts to perform a continuous advance motion. The parts are dynamically checked by a non-contacting probe arranged substantially in correspondence with a determined cross-section of the feeding rollers. The distance of the probe from the surface of the parts passing through the cross-section has a value lying within a determined range.

18 Claims, 2 Drawing Sheets

APPARATUS FOR CHECKING SURFACE FEATURES OF CONICAL PARTS INCLUDING A PROBE DISPOSED WITHIN A TRANSVERSAL GROOVE OF A ROLLER

TECHNICAL FIELD

The invention relates to an apparatus for checking features of conical parts, including support means; driving means, coupled to the support means, for supporting and rotating the conical parts, the driving means including at least two substantially cylindrical rollers coupled to the support means and defining two geometrical axes of rotation lying non parallel to each other, and motor means coupled to said cylindrical rollers for rotating them; and checking means including a probe adapted to scan the conical parts with a mutual combined motion including rotation and advance feed.

BACKGROUND ART

It is well known to carry out checkings, such as "non destructive" checkings, of mechanical parts in order to check their structural quality after machining in machine tools, such checkings being quite important in mass production in order to respond to very strict requirements relating to the reliability and safety of components subject to stresses.

In the specific case of bearing rollers it is important to check the rolling surfaces in order to detect the presence of cracks, flaws or other surface defects.

These checkings can be performed by non contacting probes, such as optical probes or eddy current probes, that detect the possible presence of determined defects on the concerned surface through mutual rotational movements between the probe and the part. In order to check all the part surface, said rotational movements are combined with mutual translation movements, thus permitting the probe to fully scan the surface. The combined mutual movements can be obtained in different ways, for example by making the parts translate and the probe rotate about the roller axis, or by making the parts rotate about their axis and the probe perform translation movements substantially parallel to the surface to be checked, etc.

Since, to a certain extent, the surface defects of the parts arise with a stochastic distribution, a sampling inspection is not sufficient, but it is necessary to inspect all the parts. For this purpose the rollers, for example coming out of a machine tool after grinding or superfinishing machining, can be displaced and guided, arranged as a row, by a conveyor towards the inspection probes, that scan the rolling surfaces.

The inspection of conical rollers is difficult due to problems for the mutual arrangement of the parts and the probes, deriving from the necessity of maintaining, during the mutual rotation and translation movements, a substantially constant distance between each probe and the surface to be checked.

U.S. Pat. No. 3,787,983, to which is referred the preamble of claim 1, discloses an apparatus for the surface inspection of conical rollers, in which the rollers are located one at a time at an inspection station, where suitable rotating supports cause their axial rotation, while stop means prevent translation displacements and an inspection probe can oscillate along a longitudinal direction. The arrangement of the rotating supports is such that the external surface of the rotating part presents, in a longitudinal section, a line parallel to the longitudinal direction, whereby a constant distance can be maintained between the probe and the surface and the probe can scan the surface.

The apparatus according to the above mentioned U.S. patent comprises a rather complex and delicate device for positioning and displacing the parts and the probe, with several elements that have to perform coordinated operations for feeding the parts, loading them between the rotating supports, displacing the parts against the stop means, closing the rotating supports against the parts, rotating the supports and simultaneously oscillating the probe, releasing the parts and ejecting them. This device must be separately actuated for the inspection of each part and therefore the operation of the apparatus is rather slow and complex. Moreover, the above mentioned steps can alter the surface state of the parts, due to wear in the rolling surface and in the surface contacting the stop means, also in view of the considerable forces applied to the part being inspected.

It is also known to transport objects by means of nonparallel rollers supporting the objects and rotating about adjacent axes.

U.S. Pat. No. 3,260,390 shows a conveyor for transporting elongate objects, such as pipes, and comprising couples of rolls (e.g. "small-size pneumatic airplane wheels") aligned along two skew axes.

The conveyor according to the U.S. patent cannot be employed for translating a row of little rollers, and, anyhow, could not guarantee a precise location of the surfaces of the rollers during their feed.

DISCLOSURE OF INVENTION

Object of the present invention is to provide an inspection apparatus for checking surface features of conical parts, without involving serious problems for the arrangement of the parts and the drawbacks of the prior art.

These and other objects and advantages are reached through an apparatus for checking surface features of conical parts, with support means; driving means, coupled to the support means, for supporting and rotating the conical parts, the driving means including rollers means defining two geometrical axes of rotation and motor means; and checking means including a probe adapted to scan the parts.

The roller means include at least two substantially cylindrical rollers, coupled to the support means so that the two geometrical axes of rotation are non parallel to each other, and defining a transversal circular groove, and are adapted to support a plurality of parts arranged substantially in a row. The roller means are rotated by the motor means and apply to the parts of the row a combined motion including rotation and forward advance. The probe is arranged fixed in the transversal groove, and the parts are checked while passing in correspondence of the groove. The main result achieved through the apparatus according to the invention is that it is possible to automatically and sequentially inspect conical parts in a quick, simple and reliable way, while the parts are displaced arranged in a row, coming out of a machine tool after relevant machining. Some of the advantages of the apparatus according to the invention consist in the use of a limited number of movable elements, with consequent better sturdiness and simplicity of operation, and in the possibility of inspecting parts having different dimensions and rolling surfaces defining different angles, through simple and quick retooling operations.

BRIEF DESCRIPTION OF THE DRAWINGS

The invention is described hereinafter with reference to the annexed drawings, given as non limiting example only, wherein.

BEST MODE FOR CARRYING OUT THE INVENTION

Figure 1:
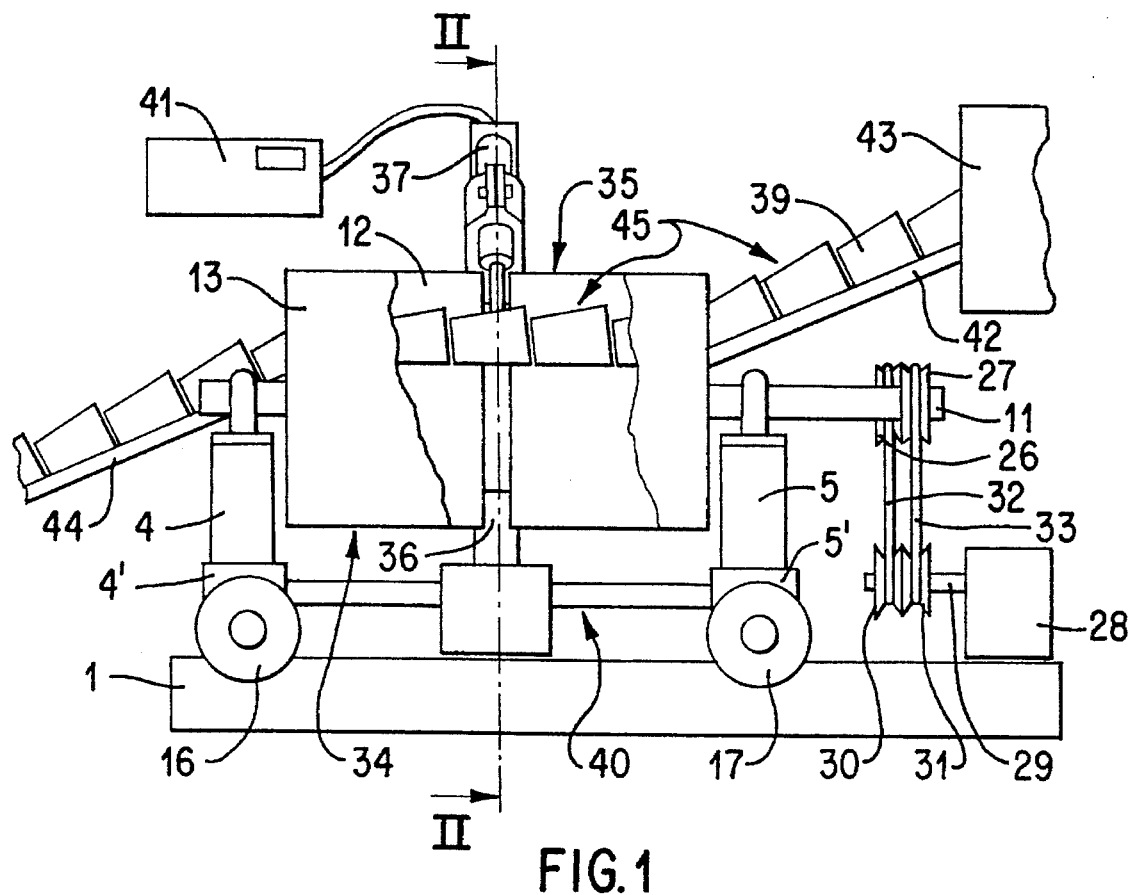
FIG. 1 is a schematic partially cutaway side view of an apparatus according to the preferred embodiment.
Figure 2:
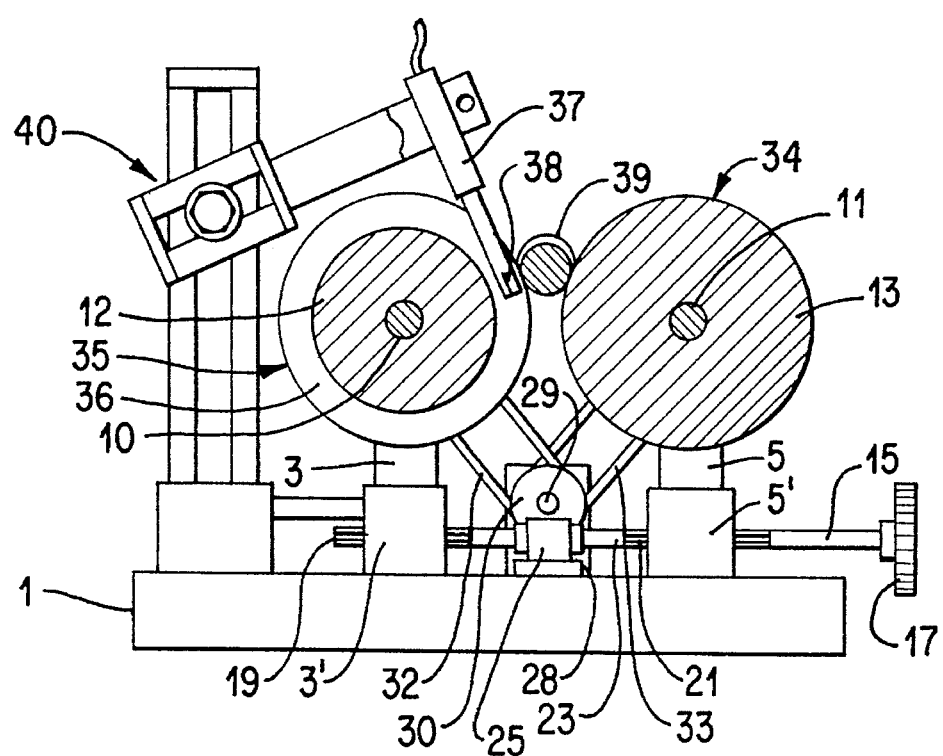
FIG. 2 is a front view of the apparatus of FIG. 1, with some details cross-sectioned according to path II—II in FIG. 1 and other details omitted for the sake of simplicity.
Figure 3:
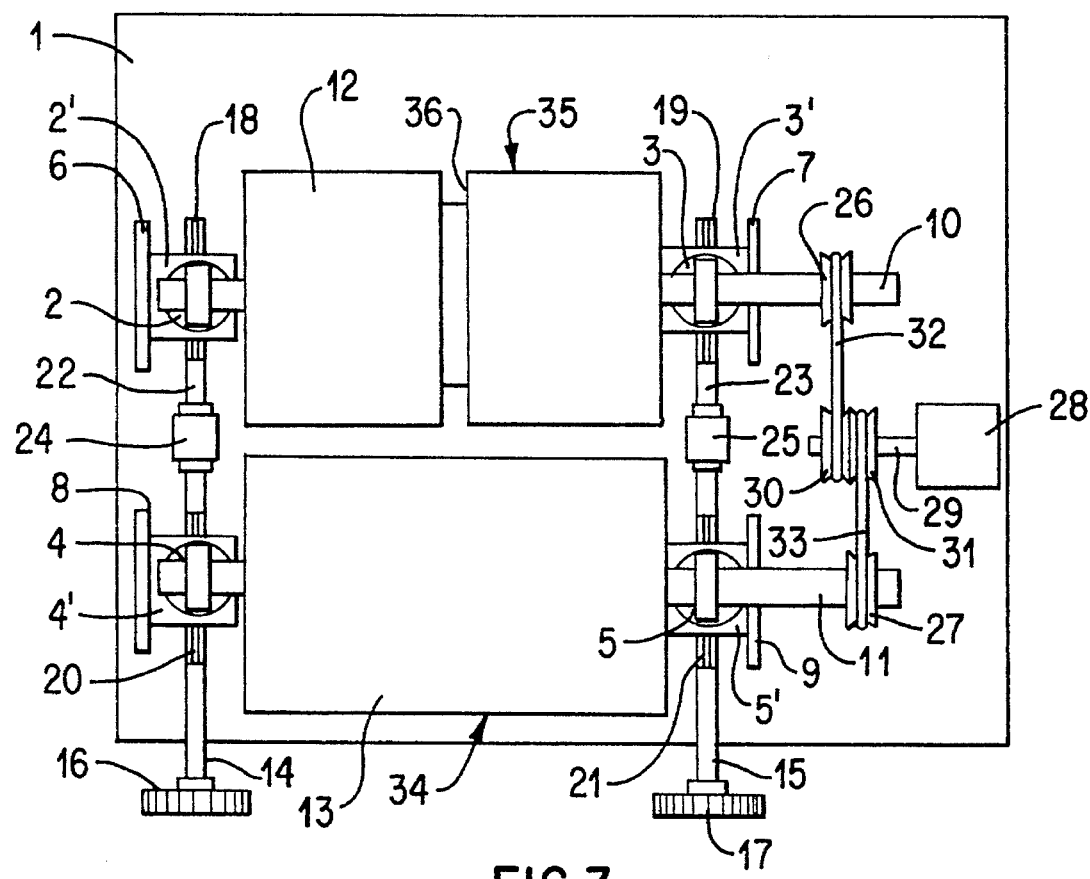
FIG. 3 is a top view of some elements of the apparatus of FIGS. 1 and 2.

The apparatus of FIGS. 1, 2 and 3 comprises support means, with a base 1 and support elements 2, 3, 4 and 5 coupled to base 1 in positions adjustable along transversal directions. Transversal guides in base 1, schematically shown in the figures and identified by reference numbers 6, 7, 8 and 9, house portions 2', 3', 3', 4' and 5' of support elements 2–5 and define the relevant adjustment directions.

Two shafts 10 and 11 are supported on elements 2, 3 and 4, 5, respectively, along two coplanar geometrical axes, parallel to base 1 and elongate along a longitudinal direction, and can freely rotate about their axes. Support elements 2–5 are schematically shown in the figures. In particular, for the sake of simplification, the following features are not illustrated in detail: the seats for shafts 10 and 11 and per se known devices (for example bearings) between the seats and the shafts for permitting rotations of the latter; devices for permitting angular displacements of the seats and of the relevant shafts supported therein with respect to portions 2'–5', for compensating variations in the arrangement of the geometrical axes of rotation; and locking devices for locking the support elements after each adjustment.

Roller means include two substantially cylindrical feeding rollers 12 and 13, which are coaxially fixed to shafts 10 and 11, respectively, for performing axial rotations about the above mentioned geometrical axes. The feeding rollers 12 and 13 have the same external diameter or slightly different diameters.

The support means also comprise adjustment means, with two pins 14 and 15, each of which is coupled to a knob 16 (17) and includes a portion with a right-hand screw thread 18 (19), a portion with left-hand screw thread 20 (21) and a central portion 22 (23), without threads but with reference surfaces. Portions 18, 19 and 20, 21 with right-hand and left-hand screw threads are respectively coupled to corresponding threaded seats of portions 2', 3' and 4', 5' of support elements 2–5.

Locking elements 24 and 25 are coupled to base 1 and house the portions 22, 23 without threads, to cause pins 14 and 15 to carry out movements of rotation only, about relevant axes.

Shafts 10 and 11 carry at respective ends pulleys 26 and 27 that rotate with the shafts. A motor 28 is secured to base 1 and is coupled to a shaft 29 carrying two coaxial pulleys 30 and 31 rotating with it. Transmission belts 32 and 33 are coupled to pulleys 26, 30 and 27, 31, respectively, and provide, with the same pulleys, motor 28 and shaft 29, driving means for rollers 12 and 13.

Rollers 12 and 13 are rotated in the same direction, in particular, with reference to FIG. 2, in clockwise direction.

Roller 13 has a cylindrical, smooth shape, is made of hard material, like steel, and defines a cylindrical feeding surface 34 with low coefficient of friction. Roller 12, too, has a substantially cylindrical surface. It can be made of hard material, with a roll covering made of a resilient material, e.g. synthetic rubber, having coefficient of friction higher than that of steel and defining a cylindrical feeding surface 35. Moreover, roller 12 defines a transversal, circular groove 36.

Checking means comprise a sensing device 37, which is partially housed in groove 36 of roller 12 and carries a probe 38, for example of the well known eddy-current type, for checking the quality of the parts 39 arranged between and supported by rollers 12 and 13. The arrangement of probe 38 in groove 36 defines a substantially transversal inspection section of the apparatus, where the parts 39 are checked.

The support means comprise an adjustable support 40, adjustably coupled to base 1 and support elements 2 and 3, that adjustably supports sensing device 37. By means of the above mentioned support 40, sensing device 37 is arranged in the transversal inspection section so that probe 38 is located in groove 36 substantially in correspondence with a zone where surface 35 of roller 12 is tangent to the part 39 that goes through the inspection section, fed due to the rotation of rollers 12 and 13, according to the operation described herebelow. In view of the coupling to support elements 2 and 3, the position of support 40 on base 1 is adjustable together with that of roller 12, in order to maintain unchanged the mutual arrangement between probe 38 and roller surface 35.

Processing and display means 41 are connected to sensing device 37 for receiving electrical signals provided by the latter and processing them to obtain information about the surface quality of the checked parts 39.

Conveyor means are schematically shown in FIG. 1 only, with a feeding chute 42 between the exit of a machine tool 43, for example a grinding machine or a finishing machine, and feeding rollers 12 and 13 and an exit chute 44, between rollers 12 and 13 and per se known collection and/or selection units, not shown in the drawings.

The operation of the apparatus illustrated in FIGS. 1, 2 and 3, for checking parts with conical shape (for example bearing rollers), is as follows.

Depending on the dimensions of the parts 39 to be checked, the mutual arrangement of rollers 12 and 13 is adjusted, in particular the mutual distance and the angular arrangement of the geometrical axes of rotation. The adjustment is carried out, through the means schematically shown and previously described, by acting on knobs 16 and 17 to cause axial rotations of pins 14 and 15 and—due to the couplings with oppositely arranged right-hand and left-hand screw threads—consequent movements for approaching or moving away from one another support elements 2, 4 and 3, 5, respectively. The possibility of adjusting the mutual position of the geometrical axes of rotation enables to define two narrow elongate zones within which the moving parts 39 and each of rollers 12 and 13 are at each instant substantially tangent.

By means of adjustable support 40 it is possible to adjust, if desired, the position of sensing device 37 and thus that of probe 38 at the transversal inspection section. However, normally these adjustments are not necessary, because the position of probe 38 with respect to roller 12 remains fixed due to the above mentioned coupling between support 40 and elements 2 and 3.

After completing the adjustment operations, shafts 10 and 11 and thus rollers 12 and 13 are caused to rotate about the respective longitudinal geometrical axes by motor 28 and the other previously described driving means. The dimensions of pulleys 26, 27, 30 and 31 and of the respective belts 32, 33 are chosen in such a way that the surface speeds of rollers 12 and 13 are equal, or the surface speed of roller 12 is slightly higher than that of roller 13.

Parts 39, aligned along a row 45 coming out of machine tool 43 after grinding or superfinishing machining, are conveyed on feeding chute 42 towards rollers 12 and 13 and loaded onto them. The contact points between parts 39 and rollers 12 and 13 lie in the above mentioned narrow elongate zones. The rotation of rollers 12 and 13 transmits to parts 39 a combined motion, of rotation about the respective geometrical axes of the parts and of substantially longitudinal advance along a feed line. The speeds of the combined movements basically depend on the surface speed of rollers 12 and 13, the mutual angular arrangement of the respective geometrical axes of the rollers 12 and 13 and the shape of parts 39.

Surface defects, if any, are detected in each part 39 by probe 38, in correspondence with the inspection section, where the parts 39, arranged in a row and with their ends in contact two by two, pass during the above mentioned combined motion. Electric signals are transmitted from probe 38 to processing and display means 41, that process them for obtaining information, e.g. as to the presence of flaws or cracks at the surface of the checked parts 39. The apparatus can comprise further sensing means, per se known and not shown in the drawings, for providing to processing means 41 a signal indicating the presence at the inspection section of a zone corresponding to adjacent ends of two parts 39 of row 45, in order to distinguish the relevant variations of the probe signal from variations due to surface defects.

In view of the described arrangement of probe 38, the distance between the probe itself and the outer surface of each conical part 39 varies within a narrow range while the part diameter at the inspection section changes during the advance of row 45. In fact, at the inspection section and at any other transversal section, a point of the surface to be checked lies within the above mentioned narrow zone defined by the contact between part 39 and roller 12 and probe 38 faces part 39 in correspondence with this zone, along a substantially radial direction of roller 12. The small oscillations of the distance and angular arrangement between probe 38 and the limited scanning area inspected at each moment by the same probe have no influence, because they are sufficiently small to enable the probe to remain within its operating range. Similar comments apply as to the limited variations of the surface speed at different points of the part surface, caused by the part diameter variations.

The speed of advance, for a certain type of part 39, is basically determined, as already mentioned, by the mutual angular arrangement of the geometrical axes of rotation of rollers 12 and 13, and thus the respective adjustment, by means of pins 14 and 15, makes it possible for probe 38 to perform a full scanning of the outer surface of each part 39, during the combined motion of the latter.

Parts 39 of row 45, at the end of the advance feed on rollers 12 and 13, are conveyed onto exit chute 44, towards the per se known collection and/or selection units.

Figure 4:
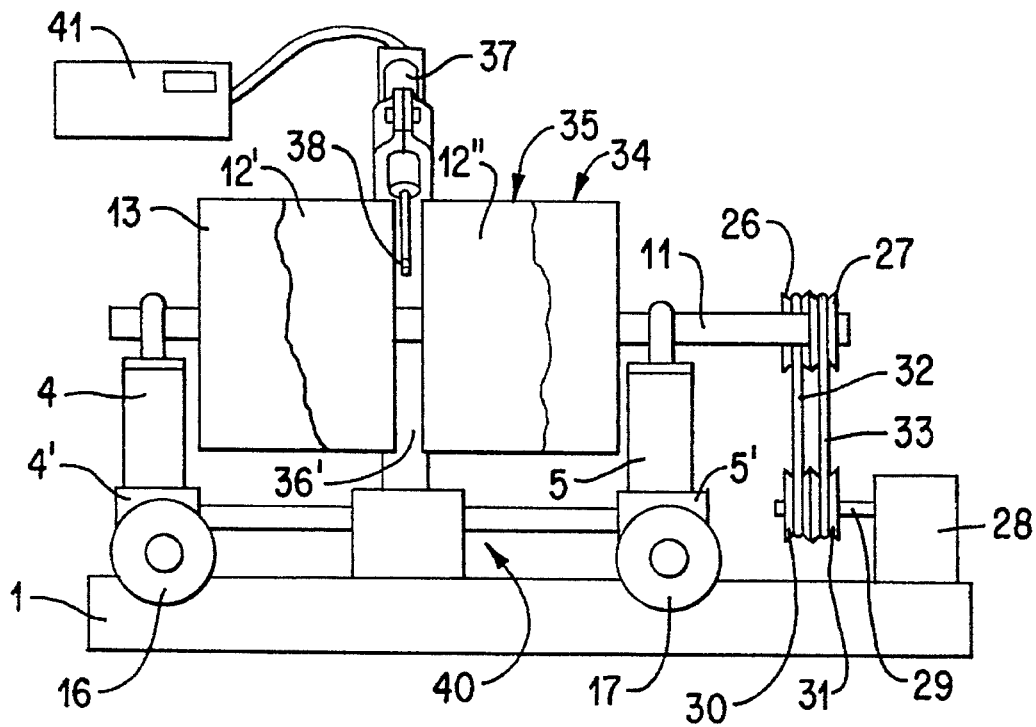
FIG. 4 is a schematic partially cutaway side view, in which some elements are omitted, of an apparatus according to another embodiment.

The apparatus illustrated in FIG. 4 (in which equal reference numbers are used for elements common with the embodiment of FIGS. 1–3) is substantially similar to that described above and is only different for the features described below.

Two cylindrical feeding rollers 12' and 12", having equal diameters, are fixed, adjacent to each other, onto shaft 10, to perform axial rotations about the respective geometrical axes. Rollers 12' and 12" define the cylindrical feeding surface 35 and are spaced apart defining a transversal circular groove consisting of a space 36' housing sensing device 37. The operation of this apparatus is quite similar to that described with reference to FIGS. 1–3.

A first prototype of an apparatus according to the invention was built for checking different types of conical bearing rollers having dimensions within the following ranges: maximum diameter between 4.5 and 25 mm; length between 8 and 30 mm; taper angle (angle between the geometrical axis and the generating lines of the conical surface) between 3 and 8 degrees. The prototype includes an eddy-current probe having a sensing surface of about 1 square mm and capable of proper operation within an angle of about ±15 degrees with respect to a central axis perpendicular to the sensing surface and with a distance from the sensing surface to the part surface between 0.2 and 0.8 mm.

The apparatus can check about seven "small" parts (maximum diameter 4.5 mm and length 8 mm) per second and two "large" parts per second.

The apparatuses according to the invention permit a dynamic checking of the surface quality of parts 39 arranged in row 45, without any need to stop the flow of these parts coming out of the machine tool, and with a high speed of the checking operations, i.e. a high number of checkings can be carried out in a short time. Moreover, since the parts 39 are simply arranged on rollers 12 (or 12' and 12") and are subjected to relatively limited forces, the risk of causing wear, scratches and the like on the surface of the part is also transcurable.

The illustrated adjustment means—or other different means permitting adjustment of the mutual position of the geometrical axes of rotation of the feeding rollers guarantee a considerable flexibility of the apparatus according to the invention, because parts 39 having different nominal dimensions and/or shape can be checked, without any need of replacing constructional elements, by simple and quick retooling operations.

Adjustable support 40 can be directly and fixedly coupled to base 1, rather than to support elements 2 and 3. In this case, if the position of rollers 12 (12' and 12") and 13 is adjusted, it is also necessary to adjust the position of sensing device 37, for arranging probe 38 (or, more exactly, for directing the electromagnetic flux generated by it) substantially in correspondence with the narrow zone of tangency between the surface 35 and the parts 39.

The probe 38 schematically illustrated in the figures can be of a type different from that specified above, for example of optical type.

Moreover, an apparatus according to the present invention can feature a plurality of inspection sections, by providing grooves in one or both of feeding surfaces 34 and 35, i.e. on the feeding rollers and/or spaces between coaxial rollers similar to the ones described above, and by arranging sensing devices 37 of different types in each groove or space. According to a particular solution, two oppositely arranged grooves and/or spaces on two rollers (12 and 13) can house two sensing devices (37) located at the same inspection section.

The scope of the present invention also includes apparatuses comprising feeding rollers rotating about mutually skew geometrical axes.

We claim:
1. An apparatus for checking surface features of conical parts (39), comprising:

support means (1–9, 14–25, 40);

driving means, coupled to the support means, for supporting, rotating, and longitudinally advancing, substantially along a feed line, conical parts (39), the driving means including at least two substantially cylindrical rollers (12, 13; 12', 12") coupled to the support means and defining two geometrical axes of rotation lying nonparallel to each other, and motor means (28–33) coupled to said rollers for rotating them; and checking means (37, 38, 41) including a stationary probe adapted to scan the conical parts during their combined motion including rotation and advance feed; and wherein said rollers are adapted to support a plurality of conical parts arranged substantially in a row and defining a transversal circular groove (36; 36'), and wherein said probe is disposed within said transversal groove, whereby the parts forming said row are checked while passing in correspondence of said transversal groove.

2. An apparatus according to claim 1, wherein said two geometrical axes of rotation are coplanar.

3. An apparatus according to claim 1, wherein the support means (1–9, 14–25, 40) comprise adjustment means (2–5, 14–25) for adjusting the position of said at least two rollers (12, 13; 12', 12") and thus the mutual position of said longitudinal axes of rotation.

4. An apparatus according to claim 1, wherein one (12) of said rollers (12, 13) defines said transversal circular groove (36).

5. An apparatus according to claim 1, wherein said at least two rollers (12, 13) are made of respective materials having different coefficients of friction.

6. An apparatus according to claim 1, wherein said at least two rollers include three rollers (12', 12"; 13), two of which are adjacent to each other and spaced apart along one of said geometrical axes of rotation, and are adapted to jointly rotate, said transversal circular groove (36') being defined between these two rollers (12', 12").

7. An apparatus according to claim 1, wherein the support means (1–9, 14–25, 40) include an adjustable support (40), for adjusting the position of said probe (37), to locate it in said transversal groove (36; 36'), at a distance from the surface of the part (39) passing in correspondence of said transversal groove (36; 36') lying within a pre-set range.

8. An apparatus according to claim 1, wherein said probe (38) is adapted to perform eddy-current checkings.

9. An apparatus according to claim 1, wherein the probe (38) is of optical type.

10. An apparatus for checking surface features of conical parts, comprising:

a support structure;

at least two substantially cylindrical rollers for simultaneously supporting a plurality of conical parts arranged substantially in a row, said rollers being rotatably supported by the support structure and defining two geometrical axes of rotation lying nonparallel to each other;

a motor coupled to said rollers for rotating them, thus causing the conical parts to perform a combined motion including rotation and advance feed substantially along a feed line; and a stationary probe carried by the support structure, for scanning the surfaces of the conical parts during said combined motion; and wherein said rollers define a transversal circular groove, and said probe is disposed within said transversal groove, whereby the conical parts forming said row are checked while passing in correspondence of said transversal groove.

11. The apparatus as recited in claim 10, wherein said two geometrical axes of rotation are coplanar.

12. The apparatus as recited in claim 10, wherein said support structure includes an adjustment device for adjusting the position of said rollers, to change the mutual position of said two geometrical axes of rotation.

13. The apparatus as recited in claim 10, wherein said transversal circular groove is defined by one of said rollers.

14. The apparatus as recited in claim 10, wherein said rollers are made of respective materials having different coefficients of friction.

15. The apparatus as recited in claim 10, wherein said rollers include three rollers, two of which are adjacent to each other and spaced apart along one of said geometrical axes of rotation, and are mutually connected to jointly rotate, said transversal circular groove being defined between said two adjacent rollers.

16. The apparatus as recited in claim 10, wherein said support structure includes an adjustable support, for adjusting the position of said probe, to set within a preset range the distance of the probe from the surface of the conical part passing in correspondence of said transversal groove.

17. The apparatus as recited in claim 10, wherein said probe is arranged to perform eddy-current checkings.

18. The apparatus as recited in claim 10, wherein said probe is of an optical type.

* * * * *